US010325068B2

(12) United States Patent
Ayed et al.

(10) Patent No.: US 10,325,068 B2
(45) Date of Patent: Jun. 18, 2019

(54) METHODS AND APPARATUS TO LABEL RADIOLOGY IMAGES

(71) Applicant: General Electric Company, Schenectady, NY (US)

(72) Inventors: Ismail Ben Ayed, London (CA); Dmitry Pavlov, Park Ridge, NJ (US); Kumaradevan Punithakumar, London (CA); Seyed-Parsa Hojjat, London (CA); Gregory Garvin, London (CA)

(73) Assignee: General Electronic Company, Schenectady, NY (US)

( * ) Notice: Subject to any disclaimer, the term of this patent is extended or adjusted under 35 U.S.C. 154(b) by 0 days.

(21) Appl. No.: 15/835,174

(22) Filed: Dec. 7, 2017

(65) Prior Publication Data

US 2018/0096101 A1 Apr. 5, 2018

Related U.S. Application Data

(63) Continuation of application No. 13/928,080, filed on Jun. 26, 2013, now Pat. No. 9,886,546.

(Continued)

(51) Int. Cl.
*G06F 19/00* (2018.01)
*G16H 30/20* (2018.01)

(52) U.S. Cl.
CPC ............ *G06F 19/321* (2013.01); *G06F 19/00* (2013.01); *G16H 30/20* (2018.01)

(58) Field of Classification Search
None
See application file for complete search history.

(56) References Cited

U.S. PATENT DOCUMENTS 7,277,564 B2 10/2007 Yarger et al.
7,462,155 B2 12/2008 England (Continued)

OTHER PUBLICATIONS

Alomari et al., "Labeling of Lumbar Discs Using Both Pixel- and Object-Level Features with a Two-Level Probabilistic Model," IEEE Transactions on Medical Imaging, vol. 30, No. 1, Jan. 2011, 10 pages.

(Continued)

*Primary Examiner* — Asher D Kells

(74) *Attorney, Agent, or Firm* — Hanley, Flight & Zimmerman, LLC

(57) ABSTRACT

Methods and apparatus are disclosed to label radiology images are disclosed. An example apparatus, includes: means for obtaining user input identifying a vertebra on a spinal image; means for generating first annotations on the spinal image based on: 1) the user input; 2) connected regions on the spinal image; and 3) a number of viewable vertebrae on the spinal image; means for generating second annotations on the spinal image based on: 1) the error; 2) second connected regions on the spinal image; and 3) the number of viewable vertebrae on the spinal image, the second connected regions on the spinal image being determined based on second contextual-information features that account for the error; means for displaying the spinal image including the second annotations; means for validating the second annotations in association with the spinal image; and means for storing the second annotations in association with the spinal image.

20 Claims, 4 Drawing Sheets

402

304

Related U.S. Application Data

(60) Provisional application No. 61/728,405, filed on Nov. 2, 2012.

(56) References Cited

U.S. PATENT DOCUMENTS 7,627,158 B2 12/2009 Hay
7,723,357 B2 5/2010 Olmarker et al.
7,906,481 B2 3/2011 Olmarker et al.
8,014,575 B2 9/2011 Weiss et al.
8,057,792 B2 11/2011 Olmarker et al.
8,067,397 B2 11/2011 Attawia et al.
8,119,127 B2 2/2012 Tobinick
8,173,694 B2 5/2012 Pepys
8,187,302 B2 5/2012 Henderson, Sr. et al.
8,236,279 B2 8/2012 Yang et al.
8,273,347 B2 9/2012 Attawia et al.
9,064,307 B2 6/2015 Ayed et al.
2002/0128715 A1 9/2002 Bryan et al.
2004/0205482 A1 10/2004 Basu et al.
2007/0174769 A1* 7/2007 Nycz .................... A61B 6/465 715/700
2007/0223799 A1 9/2007 Weiss
2008/0066019 A1 3/2008 Worek et al.
2008/0112604 A1 5/2008 Lloyd
2008/0117225 A1 5/2008 Wegenkittl et al.
2008/0132784 A1 6/2008 Porat et al.
2008/0212741 A1* 9/2008 Haras .................. A61B 5/1075 378/98
2009/0299477 A1 12/2009 Clayton et al.
2010/0145391 A1 6/2010 Kleiner
2010/0177946 A1* 7/2010 De Bruijne .......... G06K 9/6209 382/132
2011/0028825 A1 2/2011 Douglas et al.
2011/0182493 A1 7/2011 Huber et al.
2011/0225530 A1 9/2011 Osmundson et al.
2011/0228995 A1* 9/2011 Batman .................. G06T 19/00 382/128
2012/0020538 A1 1/2012 Weiss
2012/0143090 A1 6/2012 Hay et al.
2012/0172700 A1 7/2012 Krishnan et al.
2013/0035957 A1 2/2013 Gossler et al.
2014/0003684 A1 1/2014 Ayed et al.
2014/0289605 A1 9/2014 Buelow et al.
2015/0003695 A1 1/2015 Ayed et al.
2015/0173701 A1 6/2015 Major et al.

OTHER PUBLICATIONS

United States Patent and Trademark Office, “Non-final Office Action,” issued in connection with U.S. Appl. No. 13/928,080, dated Jul. 17, 2015, 13 pages.

United States Patent and Trademark Office, “Final Office Action,” issued in connection with U.S. Appl. No. 13/928,080, dated Nov. 20, 2015, 13 pages.

United States Patent and Trademark Office, “Non-final Office Action,” issued in connection with U.S. Appl. No. 13/928,080, dated May 31, 2016, 18 pages.

United States Patent and Trademark Office, “Final Office Action,” issued in connection with U.S. Appl. No. 13/928,080, dated Sep. 22, 2016, 20 pages.

United States Patent and Trademark Office, “Notice of Allowance,” issued in connection with U.S. Appl. No. 13/928,080, dated Sep. 8, 2017, 17 pages.

* cited by examiner

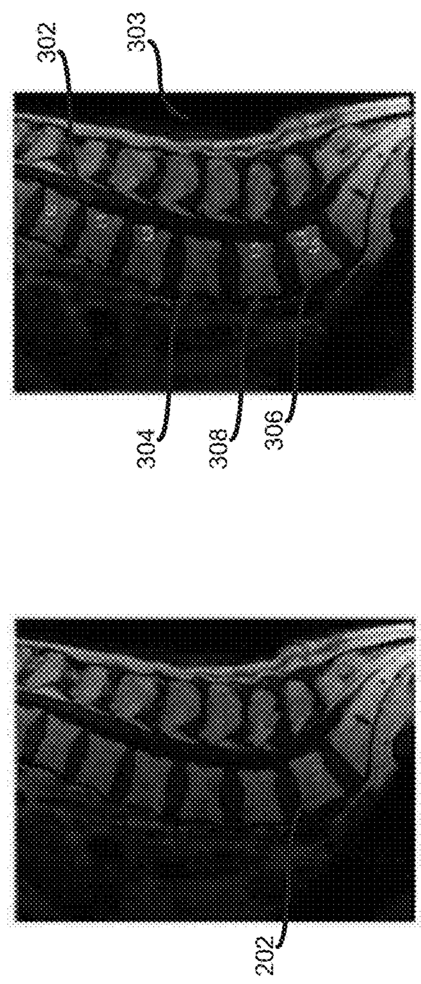
FIG. 3
FIG. 2
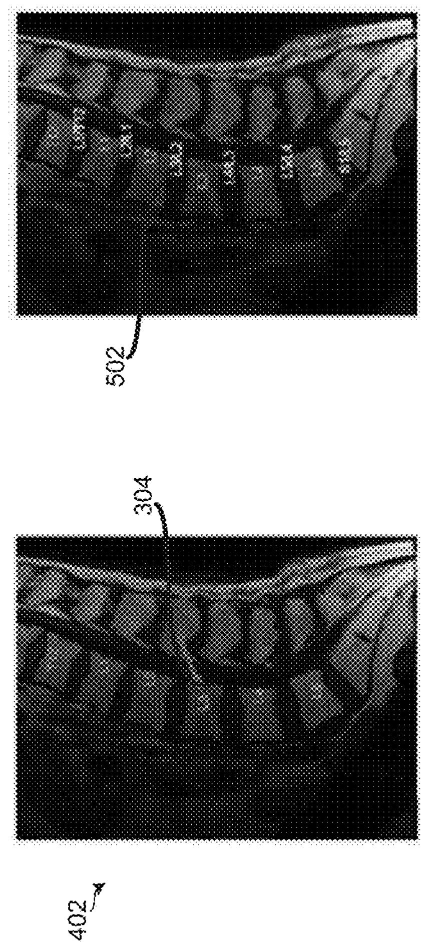
FIG. 5
FIG. 4

METHODS AND APPARATUS TO LABEL RADIOLOGY IMAGES

RELATED APPLICATION

This patent arises as a continuation of U.S. patent Ser. No. 13/928,080, filed on Jun. 26, 2013, which claims the benefit of U.S. Provisional Application Ser. No. 61/728,405, which was filed on Nov. 20, 2012. Priority is claimed to U.S. patent Ser. No. 13/928,080 and U.S. Provisional Application Ser. No. 61/728,405. U.S. patent Ser. No. 13/928,080 and U.S. Provisional Application Ser. No. 61/728,405 are hereby incorporated herein by reference in their entireties.

FIELD OF THE DISCLOSURE

This disclosure relates generally to labeling radiology images, and, more particularly, to methods and apparatus to label radiology images.

BACKGROUND

Spinal images may be obtained and used to diagnosis various spinal diseases. In some examples, these spinal images are manually annotated and/or labeled to identify the different vertebrae and/or disks. In other examples, these spinal images are automatically annotated and/or labeled to identify the different vertebrae and/or disks.

BRIEF DESCRIPTION OF THE DRAWINGS

FIGS. 2-5 are radiology images in accordance with the teachings of this disclosure being annotated by the example system of FIG. 1.

Wherever possible, the same reference numbers will be used throughout the drawing(s) and accompanying written description to refer to the same or like parts.

DETAILED DESCRIPTION

Spinal images may be annotated and/or labeled to assist in analyzing such images and/or diagnosing various spine diseases, etc. However, correctly annotating and/or labeling these images is sometimes difficult because depending on the image being viewed, the number of visible vertebrae and/or discs vary. While these variations occur, some known automated and/or semi-automated spine labeling algorithms assume that regardless of the image being viewed and the actual number of visible vertebrae and/or discs present, the number of visible vertebrae and/or discs is the same. Thus, some known spine labeling algorithms do not accurately annotate and/or label spine images in instances when not all of the vertebrae are/or discs are visible.

The examples disclosed herein relate to annotating and/or labeling spine images. To overcome some of the deficiencies encountered with some known annotating and/or labeling methods (e.g., manual or automatic), the examples disclosed herein use an example semi-automated spine annotation algorithm and/or system that annotates and/or re-annotates a spine image based on initial user input and/or subsequent user input received (e.g., feedback on non-validated annotations generated).

For example, based on initial user input (e.g., identifying a vertebra), the system can automatically provide first annotations to a spine image and present the spine image including the first annotations for user review. To quickly correct any errors included in the first annotations, the system receives user input and/or feedback with respect to the first annotations. In some examples, the user can provide input (e.g., identify new and/or improperly labeled vertebra and/or candidates) by clicking on a false positive, a false negative, a non-labeled and/or mislabeled vertebra and/or disc, etc. In response to the input and/or feedback received, the system takes into account the user input (e.g., new candidates for labeling based on user input, user identified vertebra and/or disc) and the known spatial organization of the vertebra and automatically provides second annotates and/or labels to the spine image for user review (e.g., the system re-annotates the spine image). The second annotations may correct at least one error present in the first annotations based on the user feedback received. In some examples, the user input and/or feedback is independent of the example annotation algorithm. In some examples, the system iterates and/or alternates between automatically annotating and/or labeling the spine image and receiving user input and/or feedback until the user validates the annotations and/or labels generated.

Figure 1:
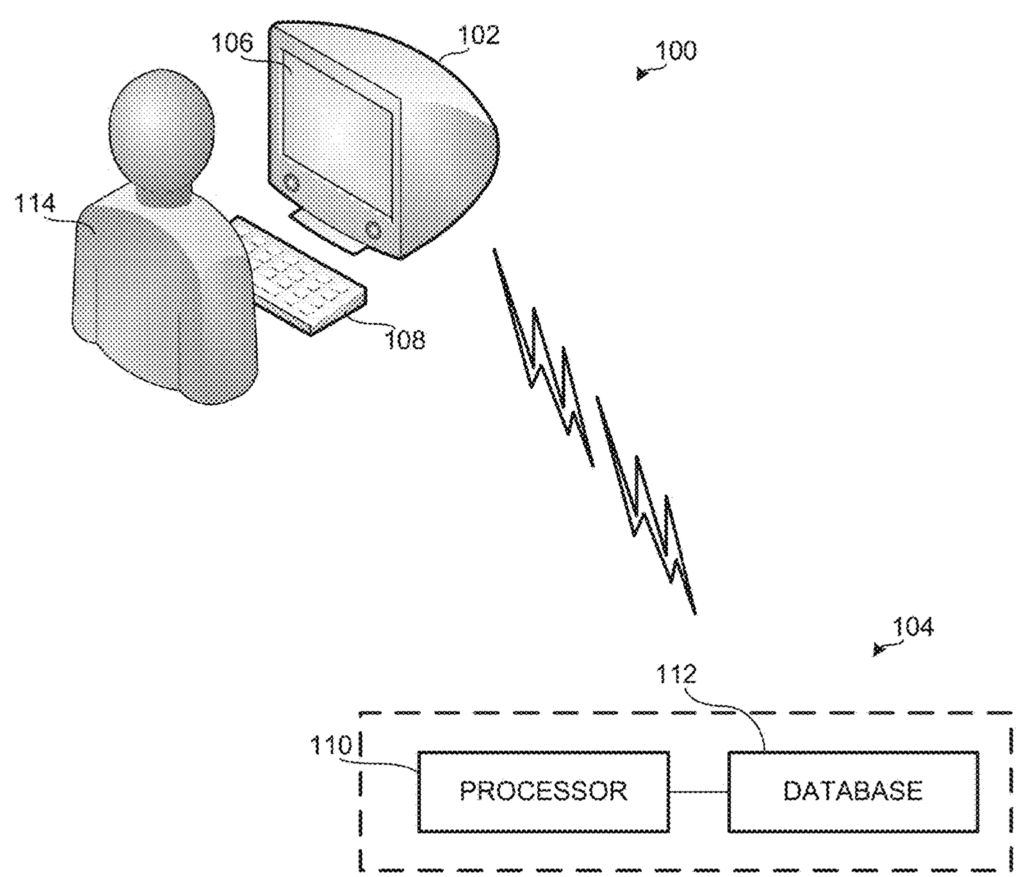
FIG. 1 is a schematic illustration of an example system to annotate radiology images.

FIG. 1 depicts an example system 100 for annotating images such as spinal images. In some examples, the system 100 includes a computer 102 and an annotator 104 communicatively coupled to the computer 102. In this example, the computer 102 includes a user interface 106 and a data input (e.g., a keyboard, mouse, microphone, etc.) 108 and the annotator 104 includes a processor 110 and a database 112.

In some examples, the user interface 106 displays data such as images (e.g., spinal images, radiology images, etc.) and/or annotated images received from the annotator 104. In some examples, the user interface 106 receives commands and/or input from a user 114 via the data input 108. For example, in examples in which the system 100 is used to annotate spinal images, the user interface 106 displays a spinal image(s) and/or an annotated spinal image(s) and the user 114 provide(s) an initial input identifying, for example, a location of a vertebra on the spinal image(s) and/or provides subsequent input identifying, for example, an error in the annotations generated on the spinal image.

In some examples, after the user interface 106 displays a spinal image (e.g., a T1-weighted MRI image, a non-annotated spinal image), the user 114 may select and/or identify a vertebra (FIG. 2, 202) using the data input 108 and, in response to receiving this user input, the annotator 104 uses the first user input to generate first annotations (FIG. 3, 302) on the spinal image (FIG. 3, 303). While the annotator 104 can generate annotations using any suitable labeling algorithm, in some examples, the annotator 104 generates the first annotations 302 from an initial set of spatially ordered points, $x_1^0, \ldots x_N^0$, where N=6 and $x_{N-1}^0$ corresponds to the L1 vertebra, $x_{N-2}^0$ corresponds to the L2 vertebra, etc.

Additionally or alternatively, in some examples, the annotator 104 generates the first annotations 302 by automatically detecting connected regions of the spinal image that are consistent with an image context of the vertebrae and selecting N—points on the spinal image that follow and/or befit the shape of the spine. In some examples, the annotator 104 automatically detects the connected regions by using data stored in the database 112 such as contextual information about spines, vertebrae and/or neighboring structures and/or other optimization and/or statistical modeling techniques (e.g., by interpolating based on statistical data and/or models), etc.).

In some examples, the connected regions may be detected by generating and/or building contextual-information features, statistical modeling the contextual information within the vertebrae and/or finding the centroids of all connected-component regions whose contextual features are consistent with the statistical model. In some examples, the contextual-information features are generated and/or built by generating a feature vector, F(p), for each point, p, in the image domain. For example, for each point, p, a 3-dimentional feature vector, $F(p)=(F_1, F_2, F_3)$, may be built, where $F_1$ is the mean intensity within a 3×10 rectangularly-shaped, vertically-oriented patch centered at point, p, $F_2$ is the mean intensity within a 10×3 rectangularly-shaped, horizontally-oriented patch centered at point, p and $F_3$ corresponds to the intensity of a pixel, p.

In some examples, the feature vector contains image statistics within several box-shaped image patches of different orientations and/or scales. Such patch-based features may encode contextual information about the vertebrae and/or neighboring structures (e.g., size, shape, orientation, relationships to neighboring structures, etc.).

In some examples, the contextual information within the vertebrae may be statistically modeled by building a multi-dimensional model distribution using all the feature vectors, F (p), within a circle and/or space centered at and/or around the first user input (e.g., the one-click user input).

In some examples, the centroids of all connected-component regions whose contextual features are consistent with the statistical model are determined by optimizing a cost function containing two constraints. In this example, the first constraint is based on a Bhattacharyya measure of similarity between feature distributions. In some examples, the first constraint substantially ensures the obtained and/or identified spinal regions are consistent with the statistical model. In this example, the second constraint is a smoothness constraint that removes small and isolated regions caused by imaging noise. In some examples, the second constraint substantially ensures that the surfaces are smooth. In some examples, K—regions of the spinal image are obtained and $[z_1, \ldots, z_K]$ are the centroids of these regions.

In some examples, N—points that follow and/or befit the shape of the spine may be selected using Equation 1 and/or by choosing N—points out of all possible combinations of N—points in the set of determined centroids, $[z_1, \ldots, z_K]$. Referring to Equation 1, $V_i$ is the vector pointing from $x_i$ to $x_{i+1}$, I=I, . . . N−1, where $V_i=x_{i+1}-x_i$.

$$[\hat{x}_1, \ldots, \hat{x}_N] = \max_{[x_1, \ldots x_{1N}] \subset [z_1, \ldots z_K]} \sum_{i=1}^{N-1} \cos(V_i, V_{i+1}) + \sum_{i=1}^{N-1} \min\left(\frac{\|V_i\|}{\|V_{i+1}\|}, \frac{\|V_{i+1}\|}{\|V_i\|}\right) \quad \text{Equation 1}$$

As shown in FIG. 3, some of the first annotations 302 generated may contain errors. For example, the first annotations 302 failed to label the L3 vertebra 304 (e.g., a false negative), the first annotations 302 labeled the L5 vertebra 306 as both L4 and L5 (false positive) and the first annotations 302 incorrectly labeled the L4 vertebra 308 as the L3 vertebra (incorrect label).

In response to reviewing the first annotations 302, the user 114 may use the input device 108 to identify one of the errors present within the first annotations 302 (e.g., a single-click correction, second user input, subsequent user input). For example, as shown in FIG. 4, the user 114 identifies and/or selects the L3 vertebra 304, which the first annotations 302 failed to label. In some examples, the annotator 104 may receive the second user input and generate second annotations 402 based on a new set of spatially ordered points, as shown in Equation 2, where $x_{new}^i$ corresponds to the coordinate vector of the new point entered by the user 114 (second user input, new candidate). In some examples, Equation 2 is solved for by choosing N points $[\hat{x}_1, \ldots, \hat{x}_N]$ out of the N+1 points in $P_i$ by enforcing Equations 2, 3, 4.

$$P_i=[x_n^i, \ldots, x_N^i, x_{new}^i] \quad \text{Equation 2}$$

Referring to Equation 3, $[\hat{x}_1, \ldots, \hat{x}_N]$ maximizes the shape-based criterion over all possible combinations of N points $[x_1, \ldots, x_N]$ in $P_i$ where $x_{new}^i \in [\hat{x}_1, \ldots, \hat{x}_N]$ ensures that the solution of Equation 3 contains the second user input. Thus, in response to receiving the second user input, the annotator 104 reassigns the labels and/or annotations 304, 306, 308 by taking into account the second user input (e.g., new candidates and/or identified vertebra) and/or the known spatial organization of the vertebrae. As shown in Equation 3, $\Sigma_{k=1}^{N-1}(\cos V_k, V_{k+1})$ is an angle constraint and $$\sum_{k=1}^{N-1} \min\left(\frac{\|V_k\|}{\|V_{k+1}\|}, \frac{\|V_{k+1}\|}{\|V_k\|}\right)$$

is a distance constraint. In some examples, the angle constraint substantially ensures that each neighboring vertebrae $[x_k, x_{k+1}, x_{x+2}]$ is almost and/or substantially aligned and the distance constraint substantially ensures that the distances between neighboring vertebrae are approximately the same.

$$[\hat{x}_1, \ldots, \hat{x}_N] = \max_{[\hat{x}_1, \ldots, \hat{x}_N] \subset P_i} \sum_{k=1}^{N-1} \cos(V_k, V_{k+1}) + \sum_{k=1}^{N-1} \min\left(\frac{\|V_k\|}{\|V_{k+1}\|}, \frac{\|V_{k+1}\|}{\|V_k\|}\right) \quad \text{Equation 3}$$

Equation 4 describes vector pointing for $x_k$ to $x_{k+1}$, $V_k$, where k=1, . . . , N−1.

$$V_k=x_{k+1}-x_k \quad \text{Equation 4}$$

As shown in FIG. 4, the second annotations 402 may be displayed via the user interface 106 for user review. In response to reviewing the second annotations 402, the user 114 may validate the second annotations 402 as being accurate or identify an additional error present within the second annotations 402 (e.g., a single-click correction, third user input, subsequent user input). If the user 114 identifies another error, the loop identified by Equation 5 is repeated until the user 114 validates the annotations.

$$i \rightarrow i+1: \text{ and } [x_1^i, \ldots, x_N^i] \rightarrow [\hat{x}_1, \ldots, \hat{x}_N] \quad \text{Equation 5}$$

If the user 114 validates the second annotations 402, the annotator 104 automatically completes the labeling of the remaining vertebrae, if any, using information from the N—vertebra labeling from Equation 3. In some examples, $[\hat{x}_1, \ldots, \hat{x}_N]$ is set to the corrected N—vertebra labeling (e.g., the vertebrae identified including the initial and subsequent user input) and the annotator 104 solves for and/or iterates Equation 6 for j–1, 2, . . . if points $2x_{N+j-1}$ and $x_{N+j-2}$ exist.

$$x_{N+j}=2x_{N+j-1}-x_{N+j-2} \quad \text{Equation 6}$$

In some examples, if $x_{N+j}$ falls within a spatial image domain, the annotator 104 assigns a label to $x_{N+j+2}$. For example, if N=6, $x_{N+1}\rightarrow$T11 for j=1, $x_{N+2}\rightarrow$T10 for j=2, $x_{N+3}\rightarrow$T9 for j=3, etc. However, if $x_{N+j}$ does not fall within the spatial image domain, the annotator 104 exits the loop of Equation 6.

In some examples, once the vertebrae are annotated and/or labeled, the annotator 104 annotates the discs 502 of the spinal image using the second annotations 402 and/or the annotations determined using Equation 6 above. In some examples, $[x_1, \ldots, x_M]$ corresponds to the completed M—vertebra labeling determined using Equation 5, where M≥N. In some examples, Equations 7 and 8 may be used to determine the coordinates of the M—discs, where disc labels are assigned to $[y_0, y_1, \ldots, y_{M-1}]$ to account for the spatial ordering of the spine discs:

$$y_0 \rightarrow \frac{S1}{L5}, y_1 \rightarrow \frac{L5}{L4}, y_2 \rightarrow \frac{L4}{L3}.$$

$$y_i = \frac{x_i + x_{i+1}}{2} \forall\, i \in [1, \ldots, M-1], \text{ and} \quad \text{Equation 7}$$

$$y_o = \frac{3x_1}{2} - \frac{x_2}{2} \quad \text{Equation 8}$$

Figure 6:
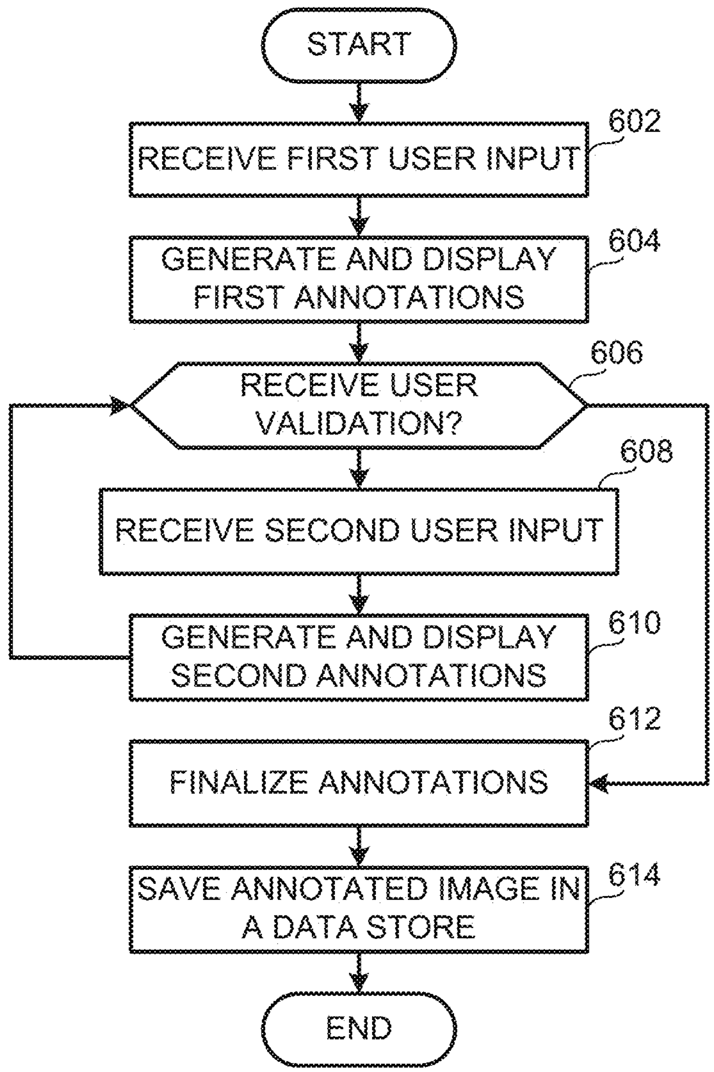
FIG. 6 is a flowchart representative of machine readable instructions that may be executed to implement the system of FIG. 1.

FIG. 6 depicts a manner of implementing the system 100 of FIG. 1. While an example manner of implementing the system of FIG. 1 has been illustrated in FIG. 6, one or more of the elements, processes and/or devices illustrated in FIG. 6 may be combined, divided, re-arranged, omitted, eliminated and/or implemented in any other way. Further, the example annotator 104, the example processor 110, the example computer 102 and/or, more generally, the example flowchart of FIG. 6 may be implemented by hardware, software, firmware and/or any combination of hardware, software and/or firmware. Thus, for example, any of the example annotator 104, the example processor 110, the example computer 102 and/or, more generally, the example flowchart of FIG. 6 could be implemented by one or more circuit(s), programmable processor(s), application specific integrated circuit(s) (ASIC(s)), programmable logic device(s) (PLD(s)) and/or field programmable logic device(s) (FPLD(s)), etc. When any of the apparatus or system claims of this patent are read to cover a purely software and/or firmware implementation, at least one of the example annotator 104, the example processor 110 and/or the example computer 102 are hereby expressly defined to include a tangible computer readable medium such as a memory, DVD, CD, Blu-ray, etc. storing the software and/or firmware. Further still, the example flowchart of FIG. 6 may include one or more elements, processes and/or devices in addition to, or instead of, those illustrated in FIG. 6, and/or may include more than one of any or all of the illustrated elements, processes and devices.

A flowchart representative of example machine readable instructions for implementing the system 100 of FIG. 1 is shown in FIG. 6. In this example, the machine readable instructions comprise a program for execution by a processor such as the processor 712 shown in the example computer 700 discussed below in connection with FIG. 7. The program may be embodied in software stored on a tangible computer readable medium such as a CD-ROM, a floppy disk, a hard drive, a digital versatile disk (DVD), a Blu-ray disk, or a memory associated with the processor 712, but the entire program and/or parts thereof could alternatively be executed by a device other than the processor 712 and/or embodied in firmware or dedicated hardware. Further, although the example program is described with reference to the flowchart illustrated in FIG. 6, many other methods of implementing the example system 100 may alternatively be used. For example, the order of execution of the blocks may be changed, and/or some of the blocks described may be changed, eliminated, or combined.

As mentioned above, the example processes of FIG. 6 may be implemented using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example processes of FIG. 6 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

The program of FIG. 6 begins at block 602 where the computer 102 receives, via the data input 108, initial input on a spine image displayed at the user interface 106 and/or stored in the database 112 (block 602). In some examples, the initial input is associated with the user 114 clicking on a vertebra of the displayed spinal image and/or labeling it manually. For example, if the L5 vertebra may be clicked (e.g., one-click, single click), identified and/or labeled by the user. In some examples, the initial user input identifying a feature and/or vertebra on the spinal image assists and/or enables the example and/or selected automated and/or semi-automated annotating algorithm to annotate and/or label the remaining vertebrae and/or discs. In some examples, the examples disclosed herein can be employed with various annotating algorithms and/or software.

At block 604, the annotator 104 generates initial spinal labeling results and/or annotations using the example and/or selected automated and/or semi-automated annotating algorithm (block 404). For example, based on the initial user input of identifying the L5 vertebra, the annotator 104 labels the L1 vertebra, the L2 vertebra, the L3 vertebra, etc. and these first annotations may be displayed at the user interface 106 for user review.

At block 606, the user 114 reviews the first annotations and the computer 102 prompts the user regarding the validity of the first annotations and/or receives a decision of whether the first annotations are valid (block 606). If the first annotation are not validated (e.g., there is at least one error present in the first annotations), the computer 102 may receive second user input relating to the error in the generated annotations (block 608). In some examples, the second user input identifies a false positive in the first annotations, a false negative in the first annotations and/or an incorrect label in the first annotations. In some examples, a false positive occurs when the annotator 104 detects a vertebra where none exists. In some examples, a false negative occurs when the annotator 104 fails to detect a vertebra. In some examples, an incorrect labeling occurs when a target vertebra is detected but assigned an incorrect label. In some examples, the user 114 identifies an error in the first annotations via a single-click correction using the data input 108. For example, if the first annotations fail to and/or incorrectly label the L3 vertebra, the user 114 can click on the L3 vertebra and/or enter a correct label for the L3 vertebra.

At block 610, second annotations are generated in response to receiving the second user input (block 610). In some examples, in response to receiving the user input, the annotator 104 automatically selects a new set of candidates (e.g., possible vertebra) and/or points on the spinal image that better fit the shape of the spine. The new set of candidates and/or points includes the initial user input, the subsequent user input, point input and/or identified by the user 114. For example, based on subsequent user input received identifying a false positive, the annotator 104 removes the point associated with the falsely identified point from the set of points. In some examples, when selecting a new set of candidates, points and/or possible vertebrae, the annotator 104 uses shape-based criterion having angel and distance constraints. In some examples, the angle constraint substantially ensures that each three neighboring vertebrae is almost and/or substantially aligned. In some examples, the distance constraint substantially ensures that the distance between neighboring vertebrae is substantially and/or approximately the same. In some examples, the annotator 104 uses the constraints, the subsequent user input (e.g., the newly identified point and/or candidate) and/or known spatial organization of the vertebrae (e.g., L1 is below T12, L2 is L1, etc.) to generate the second annotations that are more accurate than and/or remove at least one error present in the first annotations. In some examples, blocks 606, 608 and 610 are repeated and/or iterated until the user 114 validates the annotations generated and/or displayed.

At block 612, the annotator 104 finalizes the annotations (block 612). For example, the annotator 104 annotates any non-labeled vertebrae using information obtained and/or associated with generating the second annotations. In some examples, any remaining vertebrae are annotated using point coordinates for labeled vertebrae and, if the coordinates fall within a spatial image domain, the annotator 104 assigns annotations and/or labels based on the coordinates. Additionally or alternatively, the annotator 104 finalizes the annotations by annotating the discs between the vertebrae. In some examples, the discs are annotated by determining the coordinates of the discs based on the coordinates and/or annotated vertebrae and assigning labels to the discs based on the spatial ordering of the spine discs. In some examples, the annotated spine including vertebrae and disc labels is displayed to the user 114 using the user interface 106 and/or saved in the database 112 (block 614).

Figure 7:
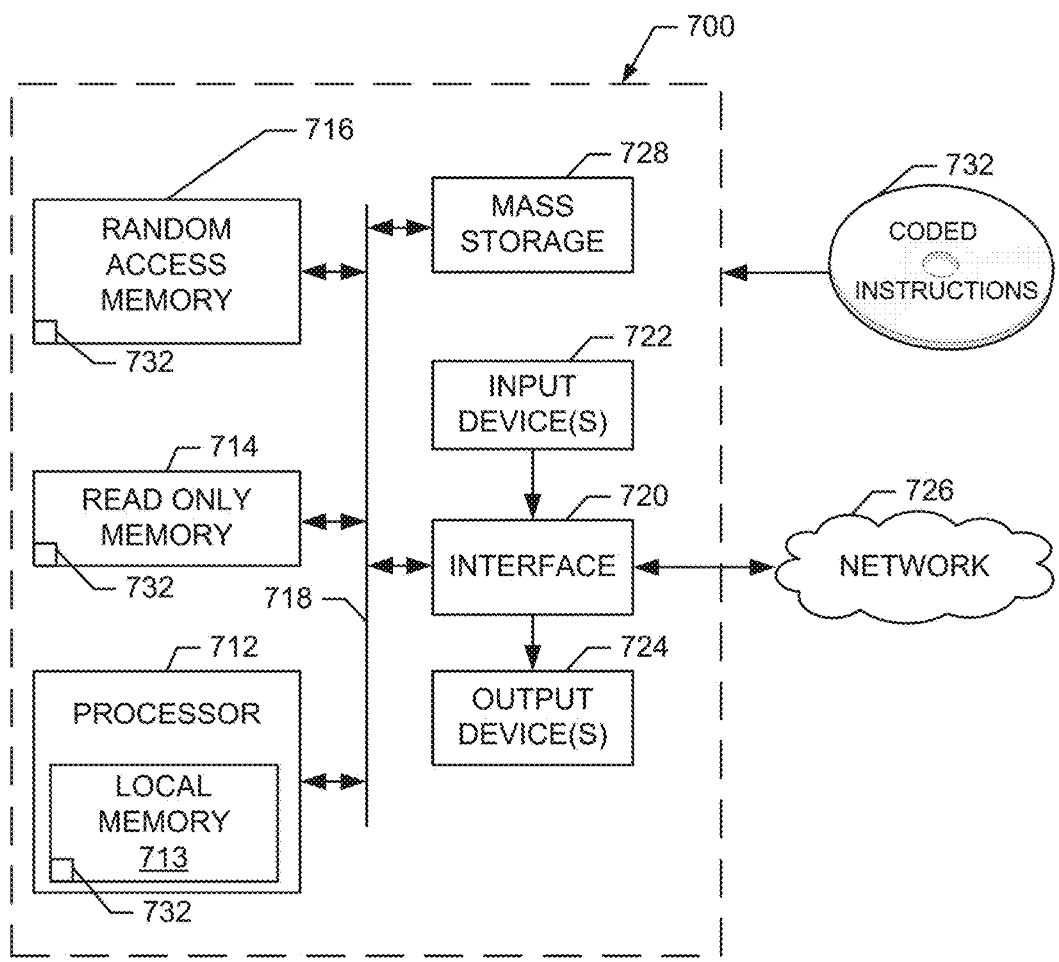
FIG. 7 is a processor platform to execute the instructions of FIG. 6 to implement the system of FIG. 1.

FIG. 7 is a block diagram of an example computer 700 capable of executing the instructions of FIG. 6 to implement the system of FIG. 1. The computer 700 can be, for example, a server, a personal computer, a mobile phone (e.g., a cell phone), a personal digital assistant (PDA), an Internet appliance or any other type of computing device.

The computer 700 of the instant example includes a processor 712. For example, the processor 712 can be implemented by one or more microprocessors or controllers from any desired family or manufacturer.

The processor 712 includes a local memory 713 (e.g., a cache) and is in communication with a main memory including a volatile memory 714 and a non-volatile memory 716 via a bus 718. The volatile memory 714 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 716 may be implemented by flash memory and/or any other desired type of memory device. Access to the main memory 714, 716 is controlled by a memory controller.

The computer 700 also includes an interface circuit 720. The interface circuit 720 may be implemented by any type of interface standard, such as an Ethernet interface, a universal serial bus (USB), and/or a PCI express interface.

One or more input devices 722 are connected to the interface circuit 720. The input device(s) 722 permit a user to enter data and commands into the processor 712. The input device(s) can be implemented by, for example, a keyboard, a mouse, a touchscreen, a track-pad, a trackball, isopoint and/or a voice recognition system.

One or more output devices 724 are also connected to the interface circuit 720. The output devices 724 can be implemented, for example, by display devices (e.g., a liquid crystal display and/or a cathode ray tube display (CRT)). The interface circuit 720, thus, typically includes a graphics driver card.

The interface circuit 720 also includes a communication device (e.g., communication device 56) such as a modem or network interface card to facilitate exchange of data with external computers via a network 726 (e.g., an Ethernet connection, a digital subscriber line (DSL), a telephone line, coaxial cable, a cellular telephone system, etc.).

The computer 700 also includes one or more mass storage devices 728 for storing software and data. Examples of such mass storage devices 728 include floppy disk drives, hard drive disks, compact disk drives and digital versatile disk (DVD) drives. The mass storage device 728 may implement the local storage device 762.

The coded instructions 732 of FIG. 6 may be stored in the mass storage device 728, in the volatile memory 714, in the non-volatile memory 716, and/or on a removable storage medium such as a CD or DVD.

From the foregoing, it will appreciate that the above disclosed methods and apparatus provide an interactive protocol that enables fast and user-friendly corrections and/or visualizations of spine annotations and/or substantially guarantees correct results in substantially all clinical scenarios. The above disclosed methods and apparatus enable annotations to be rapidly corrected independent of the choice of a labeling algorithm and/or any associated software.

An example computer-implement method disclosed herein includes generating first annotations on a spinal image. The computer implemented method also includes receiving first user input from a user on the first annotations identifying an error within the first annotations. In response to receiving the first user input, the computer implemented method also includes generating second annotations on the spinal image. The second annotations are to correct the error present within the first annotations.

In some examples, generating the first and second annotations is independent of the first input received.

In some examples, the computer implemented method also includes receiving second user input from the user validating the second annotations. In some examples, in response to the user validating the second annotations, the computer implemented method also includes generating third annotations. In some examples, the third annotations include vertebra labels and disc labels.

In some examples, the annotations include vertebrae labels.

In some examples, the first annotations are generated in response to receiving initial user input from the user identifying a vertebra on the spinal image.

In some examples, the first annotations are generated based on first spatially ordered points and the second annotations are generated based on second spatially ordered points. In some examples, the second spatially ordered points account for the first user input.

In some examples, the first annotations are generated based on an optimization model, a statistical model, or contextual information associated with a spine or vertebrae.

In some examples, generating the second annotations includes reassigning a label of a vertebra labeled by the first annotations.

An example computer readable storage medium disclosed herein includes computer program code to be executed by a processor. The computer program code, when executed, is to implement a method to annotate a spinal image. The method includes generating first annotations on a spinal image. The method also includes receiving first user input from a user on the first annotations to identifying an error within the first annotations. In response to receiving the first user input, the method also includes generating second annotations on the spinal image. The second annotations are to correct the error present within the first annotations.

In some examples, generating the first and second annotations is independent of the first input received.

In some examples, the method also includes receiving second user input from the user validating the second annotations. In some examples, in response to the user validating the second annotations, the method also includes generating third annotations. In some examples, the third annotations include vertebra labels and disc labels.

In some examples, the annotations include vertebrae labels. In some examples, the first annotations are generated based on first spatially ordered points and the second annotations are generated based on second spatially ordered points. The second spatially ordered points account for the first user input.

An example system disclosed herein includes a processor. In response to receiving a first user input via a data input, the processor is to generate first annotations on a spinal image. The processor is to also cause the spinal image having the first annotations to be displayed at a user interface. The processor is to also prompt a user to provide second user input identifying an error in the first annotations. In response to receiving the second user input, the processor is to also generate second annotations on the spinal image. The second annotations are to correct the error in the first annotations.

In some examples, the processor is to also cause the spinal image having the second annotations to be displayed at the user interface and to prompt the user to provide third user input. In some examples, the third user input validates the second annotations or identifies an error in the second annotations.

An example computer-implemented method disclosed herein includes a) obtaining user input identifying a point corresponding to a vertebra on a spinal image. In response to the user input, the computer-implemented method also includes b) using the user input to determine a number of viewable vertebrae on the spinal image. The computer-implemented method also includes c) identifying points on the spinal image corresponding to respective vertebrae based on the determined number of viewable vertebrae. The computer-implemented method also includes d) generating annotations on the spinal image corresponding to each of the determined number of viewable vertebrae. The annotations anatomically label and distinguish between two or more immediately adjacent vertebrae on the spinal image using contextual-information feature vectors. The contextual-information feature vectors encode the identified points with information of at least one of size, shape, orientation, or relationships to neighboring structures. The computer-implemented method also includes e) receiving a first subsequent user input on the previously generated annotations identifying a point corresponding to an error within the previously generated annotations. In response to receiving the first subsequent user input, the computer-implemented method also includes f) updating the identified points and contextual-information feature vectors for the updated identified points, automatically generating subsequent annotations on the spinal image using the updated contextual-information feature vectors. The subsequent annotations correcting the error present within the previously generated annotations. The computer-implemented method also includes g) receiving a second subsequent user input. When the second subsequent user input identifies an error within the previously generated annotations, the computer-implemented method also includes repeating e)-g). When the received second subsequent user input does not identify an error within the previously generated annotations, the computer-implemented method also includes validating the previously generated annotations in association with the spinal image, and storing in a database the previously generated annotations in association with the spinal image.

In some examples, generating the annotations and the subsequent annotations is independent of the first subsequent user input received.

In some examples, the computer-implemented method also includes receiving the second subsequent user input from the user validating the previously generated annotations. In some examples, in response to validating the previously generated annotations, the computer-implemented method also includes generating second subsequent annotations. The second subsequent annotations include vertebra labels and disc labels.

In some examples, the annotations include vertebra labels.

In some examples, the annotations are generated based on first spatially ordered points and the subsequent annotations are generated based on second spatially ordered points. The second spatially ordered points account for the first subsequent user input.

In some examples, the annotations are generated based on an optimization model, a statistical model, or contextual information associated with a spine or vertebrae.

In some examples, generating the subsequent annotations includes reassigning a label of a vertebra labeled by the annotations.

In some examples, prior to the obtaining of the user input, no vertebrae are identified on the spinal image, and no annotation suggestion is provided.

A non-transitory computer readable storage medium disclosed herein includes computer program code to be executed by a processor. The computer program code, when executed, is to implement a method to annotate a spinal image. The method includes a) obtaining user input identifying a point corresponding to a vertebra on a spinal image. In response to the user input, the method also includes b) using the user input to determine a number of viewable vertebrae on the spinal image. The method also includes c) identifying points on the spinal image corresponding to respective vertebrae based on the determined number of viewable vertebrae. The method also includes d) generating annotations on the spinal image corresponding to each of the determined number of viewable vertebrae. The annotations anatomically label and distinguish between two or more immediately adjacent vertebrae on the spinal image using contextual-information feature vectors. The contextual-information feature vectors encode the identified points with information of at least one of size, shape, orientation, or relationships to neighboring structures. The method also includes e) receiving a first subsequent user input on the previously generated annotations identifying a point corresponding to an error within the previously generated annotations. In response to receiving the first subsequent user input, the method also includes f) updating the identified points and contextual-information feature vectors for the updated identified points, automatically generating subsequent annotations on the spinal image using the updated contextual-information feature vectors. The subsequent annotations correcting the error present within the previously generated annotations. The method also includes g) receiving a second subsequent user input. When the second subsequent user input identifies an error within the previously generated annotations, the method also includes repeating e)-g). When the received second subsequent user input does not identify an error within the previously generated annotations, the method also includes validating the previously generated annotations in association with the spinal image, and storing in a database the previously generated annotations in association with the spinal image.

In some examples, generating the annotations and the subsequent annotations is independent of the first subsequent user input received.

In some examples, the method also includes receiving the second subsequent user input from the user validating the previously generated annotations. In some examples, in response to validating the previously generated annotations, the method also includes generating second subsequent annotations. In some examples, the second subsequent annotations include vertebra labels and disc labels.

In some examples, the annotations include vertebrae labels.

In some examples, the annotations are generated based on first spatially ordered points and the subsequent annotations are generated based on second spatially ordered points. The second spatially ordered points account for the first subsequent user input.

A system disclosed herein includes a processor to a) obtain a user input, via a data input, identifying a point corresponding to a vertebra on a spinal image. In response to the user input, the processor is to also b) use the user input to determine a number of viewable vertebrae on the spinal image. The processor is to also c) identify points on the spinal image corresponding to respective vertebrae based on the determined number of viewable vertebrae. The processor is to also d) generate annotations on the spinal image corresponding to each of the determined number of viewable vertebrae. The annotations anatomically label and distinguish between two or more immediately adjacent vertebrae on the spinal image using contextual-information feature vectors. The contextual-information feature vectors encode the identified points with information of at least one of size, shape, orientation, or relationships to neighboring structures. The processor is to also e) to cause the spinal image having the annotations to be displayed at a user interface. The processor is to also prompt a user to provide first subsequent user input identifying a point corresponding to an error in the previously generated annotations. In response to receiving the first subsequent user input, the processor is also to f) update the identified points and contextual-information feature vectors for the updated identified points. The processor is also to automatically generate subsequent annotations on the spinal image using the updated contextual-information feature vectors in response to receiving the first subsequent user input. The subsequent annotations to correct the error in the previously generated annotations. The processor is to also g) receive second subsequent user input. When the second subsequent user input identifies an error within the previously generated annotations, the processor is to also repeat e)-g). When the second subsequent user input does not identify an error within the previously generated annotations, the processor is to also validate the previously generated annotations in association with the spinal image, and cause the previously generated annotations to be stored in a database in association with the spinal image.

In some examples, the processor is to also cause the spinal image having the subsequent annotations to be displayed at the user interface and to prompt the user to provide second subsequent user input.

It is noted that this patent claims priority from U.S. Provisional Application Ser. No. 61/728,405, which was filed on Nov. 20, 2012, and is hereby incorporated herein by reference in its entirety. It is noted that this patent claims priority to U.S. patent Ser. No. 13/928,080, filed on Jun. 26, 2013 and is hereby incorporated herein by reference in its entirety.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus, comprising:

means for obtaining user input identifying a vertebra on a spinal image;

means for generating first annotations on the spinal image based on: 1) the user input; 2) connected regions on the spinal image; and 3) a number of viewable vertebrae on the spinal image, the connected regions on the spinal image being determined based on contextual-information features that account for the user input, the contextual-information features including information about the viewable vertebrae or information about neighboring structures, the number of viewable vertebrae being determined from the contextual-information features;

means for identifying an error in the first annotations;

means for generating second annotations on the spinal image based on: 1) the error; 2) second connected regions on the spinal image; and 3) the number of viewable vertebrae on the spinal image, the second connected regions on the spinal image being determined based on second contextual-information features that account for the error;

means for displaying the spinal image including the second annotations;

means for validating the second annotations in association with the spinal image; and means for storing the second annotations in association with the spinal image.

2. The apparatus of claim 1, wherein the contextual-information features are generated based on feature vectors for points in an image domain.

3. The apparatus of claim 2, further including:

means for generating a model using the feature vectors and associated with the user input;

means for identifying the contextual-information features that are consistent with the model;

means for identifying centroids of the connected regions on the spinal image of the contextual-information features that are consistent with the model; and means for selecting first points that form a shape of a spine on the spinal image from the centroids.

4. The apparatus of claim 3, wherein the means for identifying the error in the first annotations include means for identifying an error in the shape of the spine.

5. The apparatus of claim 4, wherein the error in the shape of the spine includes a vertebra on the spinal image not corresponding to one of the first annotations.

6. The apparatus of claim 4, wherein the means for generating the second annotations includes means for selecting second points that correct for the error in the shape of the spine relative to the first points, the second points including second user input identifying the error in the first annotations.

7. The apparatus of claim 6, wherein the second user input corresponds to a coordinate vector of a point in the image domain.

8. The apparatus of claim 2, wherein the means for generating the second annotations includes means for maximizing a shape-based criterion associated with the points based on second user input identifying the error in the first annotations.

9. The apparatus of claim 8, wherein the shape-based criterion includes an angle constraint associated with vertebrae alignment on the spinal image and a distance constraint associated with vertebrae spacing.

10. The apparatus of claim 8, wherein the means for maximizing the shape-based criterion associates distances between adjacent vertebrae on the spine that are approximately the same in accordance with the shape-based criterion.

11. A system, comprising:

a processor to:

identify a vertebra on a spinal image;

generate first annotations on the spinal image based on: 1) user input; 2) connected regions on the spinal image; and 3) a number of viewable vertebrae on the spinal image, the connected regions on the spinal image being determined based on contextual-information features that account for the user input, the contextual-information features including information about the viewable vertebrae or information about neighboring structures, the number of viewable vertebrae being determined from the contextual-information features;

identify an error in the first annotations;

generate second annotations on the spinal image based on: 1) the error; 2) second connected regions on the spinal image; and 3) the number of viewable vertebrae on the spinal image, the second connected regions on the spinal image being determined based on second contextual-information features that account for the error;

display the spinal image including the second annotations;

validate the second annotations in association with the spinal image; and store the second annotations in association with the spinal image.

12. The system of claim 11, wherein the contextual-information features are generated based on feature vectors for points in an image domain.

13. The system of claim 12, wherein the processor is to generate a model using the feature vectors and associated with the user input, and wherein the processor is to identify the contextual-information features that are consistent with the model.

14. The system of claim 13, wherein the processor is to identify centroids of the connected regions on the spinal image of the contextual-information features that are consistent with the model.

15. The system of claim 14, wherein the processor is to optimize a cost function including a first constraint associated with a Bhattacharyya measure of similarity between feature distributions and a second constraint associated with removing regions associated with image noise.

16. A tangible machine-readable storage medium comprising instructions which, when executed, cause a processor to at least:

obtain user input identifying a vertebra on a spinal image;

generate first annotations on the spinal image based on: 1) the user input; 2) connected regions on the spinal image; and 3) a number of viewable vertebrae on the spinal image, the connected regions on the spinal image being determined based on contextual-information features that account for the user input, the contextual-information features including information about the viewable vertebrae or information about neighboring structures, the number of viewable vertebrae being determined from the contextual-information features;

identify an error in the first annotations;

generate second annotations on the spinal image based on: 1) the error; 2) second connected regions on the spinal image; and 3) the number of viewable vertebrae on the spinal image, the second connected regions on the spinal image being determined based on second contextual-information features that account for the error;

display the spinal image including the second annotations;

validate the second annotations in association with the spinal image; and store the second annotations in association with the spinal image.

17. The tangible machine-readable storage medium of claim 16, wherein the contextual-information features are generated based on feature vectors for points in an image domain.

18. The tangible machine-readable storage medium of claim 17, wherein the feature vectors include image statistics associated with image patches of different orientations or scales.

19. The tangible machine-readable storage medium of claim 18, wherein the image patches encode the information about the viewable vertebrae or the information about the neighboring structures.

20. The tangible machine-readable storage medium of claim 19, wherein the information includes at least one of size, shape, orientation, or relationships to neighboring structures.

* * * * *